United States Patent [19]

König et al.

[11] 3,953,417

[45] Apr. 27, 1976

[54] SYNTHETICALLY MODIFIED TRYPSIN INHIBITORS AND PROCESS FOR PREPARING THEM

[75] Inventors: Wolfgang König, Langenhain, Taunus; Oswald Zwisler, Marburg-Marbach; Gerhard Guthorlein, Cappel, all of Germany

[73] Assignee: Hoechst Aktiengesellschaft, Frankfurt am Main, Germany

[22] Filed: Sept. 4, 1974

[21] Appl. No.: 503,066

[30] Foreign Application Priority Data

Sept. 6, 1973 Germany............................ 2344886

[52] U.S. Cl............................ 260/112.5 R; 424/177
[51] Int. Cl.²................... C07C 103/52; C08H 1/00
[58] Field of Search...................... 260/112.5, 112.7

[56] References Cited
UNITED STATES PATENTS

| | | |
|---|---|---|
| 3,558,773 | 1/1971 | Schultz.............................. 260/112.5 |
| 3,798,205 | 3/1974 | Werle et al....................... 260/112.5 |
| 3,847,893 | 11/1974 | Brandenburg et al........... 260/112.7 |

*Primary Examiner*—Lewis Gotts
*Assistant Examiner*—Reginald J. Suyat
*Attorney, Agent, or Firm*—Henry W. Koster

[57] ABSTRACT

Modified trypsin-callicrein inhibitor wherein the five carboxyl groups present in the unmodified material are amidated by $$-(R)(R)_xW \text{ groups,}$$

wherein R is prolyl or

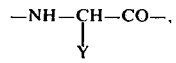

X is an integer from 1 to 10, Y is hydrogen, alkyl, or substituted alkyl and W is $-OH$, $-NH_2$, $-NHC_2H_5$, $-OCH_3$, or $-OC_2H_5$. Method for making trypsin-callicrein inhibitor so modified by amidation.

2 Claims, No Drawings

SYNTHETICALLY MODIFIED TRYPSIN INHIBITORS AND PROCESS FOR PREPARING THEM

Many organs of mammals, especially the lung of bovines, contain a trypsin-callicrein inhibitor which can be isolated therefrom in various ways and which has been used now for 15 years with great success as a polyvalent proteinase and esterase inhibitor in the therapy of enzyme disorders.

This trypsin-callicrein inhibitor is a basic polypeptide with a molecular weight of 6500 and an isoelectric point of about 10.5. It consists of a single peptide chain of 58 amino-acids, the primary structure of which is known from Biochemical and Biophysical Research Communications Vol. 20, pages 463 to 468 (1965) and which is cross-linked by 3 disulfide bridges.

The high therapeutic value of this inhibitor is that it inhibits various proteinases and esterases, for example trypsin, chymotrypsin, cathepsin, plasmin and callicrein. For this purpose, often considerable amounts of the inhibitor are injected, mainly intravenously. It has been found that the inhibitor is stored after a relatively short time, preferably in the kidneys of the test animal or of the human. It is assumed today that this is because the strongly basic inhibitor molecule is bound in unspecific manner to acid muco-polysaccharides or nucleic acids. Only 1.5 % of the native inhibitor are excreted with the urine; in order to make possible excretion of the preponderant residual quantity, the organism first degrades an amino-acid each (arginine or alanine) bound to an amino and carboxyl group, the inhibitor aggregates to a higher molecular form and is only then eluted very slowly from the kidney.

Tests with a chemically modified inhibitor in which a maleoyl group had been introduced over all free amino groups and which proved to be inactive demonstrated that this substance, the isoelectric point of which was considerably lower, was eluted essentially faster from the kidney and could be excreted with the urine. Thus, an inhibitor having full biological activity and a lower isoelectric point would have considerable value. Now, in principle it is possible to reduce positive charges by acylation of the free amino group and thus to lower the isoelectric point. However, all these reactions yield a reaction product with reduced activity, if not even an inactive product, since the 5 amino groups of the molecule must be assigned to 4 equivalent ε-amino groups of the lysine and 1 α-amino group, while, on the other hand, the lysine in position 15 is decisive for the inhibitor action of the substance. Substitution of the amino group of lysine 15 causes the loss of the biological activity.

Now, it has been found that, unexpectedly, the activity of the inhibitor is only slightly modified or not at all by prolongation of the 5 present carboxyl groups with acid peptides, but that because of the lowering of the isoelectric point the modified inhibitor is excreted much faster from the kidney than an unmodified molecule.

Thus, the present invention provides semi-synthetically prepared derivatives of the basic trypsin-callicrein inhibitor from organs of mammals, in which the 5 carboxyl groups present in the peptide molecule are amidated by peptide groups of the general formula I

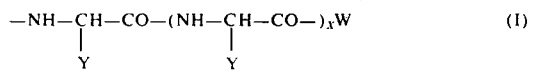 (I)

in which X represents an integer from 0 to 10, Y represents hydrogen or a straight chain or branched alkyl radical of 1 to 5 carbon atoms which may be substituted by a carboxyl, hydroxyl or carbonamide group, the group

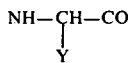

may also represent proline. If X = O, Y represents —$CH_2COOH$ or —$CH_2$-$CH_2$-COOH, and if X is an integer from 1 to 10, at least one lateral chain of Y is —$CH_2$-COOH or —$CH_2$-COOH. W represents —OH, but in the presence of at least two carboxyl groups in the lateral chains, it may also represent —$NH_2$, NH-$C_2H_5$, —$OCH_3$ or $OC_2H_5$.

The invention furthermore relates to a process for preparing the above-specified peptides, which comprises reacting the trypsin-callicrein inhibitor, whose 5 primary amino groups are protected by protective groups that can easily be split off with acids, with amino-acids or peptides of the general formula II

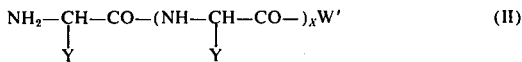 (II)

in the presence of 1-hydroxy-benzotriazole and dicyclohexylcarbodiimide and subsequently splitting off the protective groups with the aid of acids. Y and X have the meanings given above, the carboxyl groups in Y, however, are present as tert.butyl esters. W' represents tert.butoxy, but if at least 2 tert.butyl ester groups are present in the lateral chains, then W' may also represent —$NH_2$, —NH-$CH_3$, —NH-$C_2H_5$, —$OCH_3$ or $OC_2H_5$.

In order to be able to modify the trypsin-calicrein inhibitor at its carboxyl groups, it is suitable to block the amino groups by amino-protective groups which can be easily split off with acids, for example tert. alkoxy-carbonyl groups. The introduction of the often used Boc-group can be carried out in various ways. Thus, the Boc-groups can be introduced with Boc-azide as well as with Boc-active esters, for example the p-nitrophenyl ester or the N-hydroxysuccinimide ester. In all cases, a product is formed which is uniform in paper electrophoresis. These N-protected compounds are reacted in the presence of 1-hydroxy-benzotriazole and dicyclohexylcarbodiimide with a compound of the general formula II in dimethylformamide or dimethylacetamide. The protective groups are split off with trifluoroacetic acid or HCl/glacial acetic acid and the raw product is either dialyzed or chromatographed over Sephadex G 25$^{(R)}$, a cross-linked dextran gel. For further purification, it is advisable also to chromatograph the dialyzed product likewise over Sephadex G 25$^{(R)}$ or to subject it to partition chromatography on Sephadex LH 20$^{(R)}$, a cross-linked akylated dextran gel.

In order to lower the isoelectric point of the trypsin-callicrein inhibitor, the amino-acid rest or peptide or peptide group to be condensed must contain at least two carboxyl groups. Among the naturally occurring amino-acids, only aspartic acid and glutamic acid in their L- or D-form may be used. With dipeptides and higher peptides it is also possible to introduce, in addition to the acid amino-acids, other aliphatic amino-acids, for example glycine, alanine, leucine, valine, isoleucine, serine, threonine, asparagine, glutamine or proline in their L- or D-form. It is preferred, however, witth higher peptides also to use aspartic acid and glutamic acid as pepttide components. If two or more carboxyl groups are present in the form of tert. butyl esters in the peptide to be condensed, further carboxyl groups in the form of amides or alkyl esters may also be present. After acid treatment with trifluoroacetic acid or HCl/glacial acetic acid, there are obtained in this manner trypsin inhibitors which, besides a low isoelectric point, additionally have amide groups or alkyl ester groups.

In order to prove the decrease of the basic character and the increase of the acid character in the inhibitor derivatives prepared according to the invention, the native inhibitor and modified preparations were subjected to micro-zone electrophoresis on cellulose-acetate foil in a diethyl-barbiturate buffer of pH 8.6.

TThe native inhibitor migrates in tthiis case towards the cathode, whereas the modified preparations migrate, depending on the modified group, more or less far towards the anode. For the native inhibitor, the migration distance towards the cathode is about 3 mm. For the modified preparation, in which the modified groups in the individual cases contain 1, 2, 3 or 4 acid amino-acids, the migration distances towards the anode are about 1.5 mm, 8 mm, 13.5 mm and 17 mm respectively.

Thus, the modification of the inhibitor leads to preparations the basic character of which is reduced and the acid character of which is increased. Modification with one group containing a single acid amino-acid already leads to such a lowering of the isoelectric point that at pH 8.6 the acid character slightly surpasses tthe basic character.

The isoelectric points estimated from the dissociation constants of the functional groups of the inhibitor and its derivatives prepared according to the invention are about 10.5 for the native inhibitor and about 8.1, 4.6, 4.35 and 4.1 for the modified preparations, the modified group containing one, two, three or four acid amino-acids.

For the fluoroescence-microscopical proof of the storage of inhibitor and modified inhibitor in the kidneys, 3 rabbits each having a weight of 2.5 kg were injected intravenously at the same time with 20 mg of native inhibitor and 20 mg of inhibitor modified according to the invention, respectively. After 2 days, the kidneys were removed, cut and incubated with a fluorescein-marked γ-globulin preparation which had been obtained from the anti-serum of rabbits which had previously been vaccinated several times with inhibitor and adjuvant according to Freund in order to increase antibody formation.

The following picture was observed under the fluorescence-microscope: all kidney sections of the animals treated with the native inhibitor showed great, partly confluing fluorescent spots distributed over the whole visual field, whereas the sections of the kidneys of those animals that had obtained the modified inhibitor in most cases showed no fluorescence and contained small fluorescent spots only in a few cases. This test showed in distinct manner that the inhibitor with lowered isoelectric point is much less stored or not at all stored in the kidneys.

In preliminary tests by double diffusion, it had been confirmed that the antibody preparation used reacted not only towards the native inhibitor but also towards the reaction products thereof obtained according to the invention.

In order to determine the activity of the modified trypsin-callicrein inhibitors, the following method was used:

The inhibitor solution was pre-incubated with a determined amount (corresponding to a determined activity) of trypsin solution; after a short time, a suitable trypsin substrate, for example N-benzoyl-arginine-4-nitroanilide (BAPA) was added and after some time and after having stopped the reaction, the yellow coloration due to p-nitroaniline released by uninhibited trypsin was measured quantitatively on a photometer at a suitable wave length, for example at 405 m$\mu$.

In particular, this process was carried out in that a quantitiy of trypsin (trypsin, crystallized, analytically pure) which, as previously determined, when combined within 30 minutes at 37°C with BAPA, causes a certain extinction at 405 m$\mu$, was incubated with increasing amounts of the inhibitor in a constant volume. After a pre-incubation of 30 minutes, the standard amount of BAPA was added. The reaction was stopped after 30 minutes at 37°C of BAPA incubation by the addition of dilute acetic acid and the yellow coloration was measured. When plotting in a diagram the inhibitor quantities added against the corresponding extinction values, a cuve was obtained from which it was easy to determine which quantity of inhibitor added was able to inhibit the trypsin, which had always been added in constant amounts, by one half, Since it was known which activity or what amount of trypsin had been added, it could be recalculated how many mg of inhibitor were able to inhibit how much of trypsin.

In this test, about 1 mg of the modified inhibitor was found to be able to inactivate about 3 mg of trypsin.

The trypsin-callicrein inhibitor modified according to the invention serves as a medicament in the treatment of hermorrhages caused by excessive fibrinolysis, for example in surgery in the case of prostate bleeding or disorders during the healing of wounds, in internal medicine as additional therapy in cases of hemophilia, in gynecology in cases of placenta praevia, fetal deatth in utero and atonic after-bleeding, and for prophylaxis in the case of operations of parenchymatous organs, as well as in cases of prostatectomies and fat embolisms.

The new medicaments of the invention are injected intravenously in sterile isotonic solution or administered as a slow drip infusion after dilution in infusion solutions, for example physiological salt solution. As doses, there may be administered 0.15 to 3 mg per kg.

The following Examples illustrate the invention.

EXAMPLE 1

Trypsin-callicrein inhibitor penta-L-glutamic acid 284 mg of DCC were added at 0°C to a suspension of 900 mg of penta-Boc-trypsin-callicrein inhibitor, 386 mg (1.3 mmoles) of Hcl.H-Glu(OBu$^t$)-OBu$^t$, 175 mg (1.3 mmoles) of HOB+ and 0.17 ml (1.3 mmoles) of N-ethylmorpholine in 10 ml of dimethylformamide and the whole was stirred for 1 hour at 0°C and 24 hours at room temperature. The precipitate was filtered off with suction and the filtrate was concentrated. The residue was triturated with ether and dried. Yield: 1.39 g.

The substance so obtained was dissolved in 10 ml of trifluoroacetic acid. The solution was allowed to stand for 30 minutes at room temperature and subsequently concentrated under reduced pressure. The residue was triturated with ether and filtered off with suction. Yield: 1.17 g.

The substance so obtained was dialyzed against water and freeze-dried. Yield: 710.3 mg.

325 mg of the dialyzed and freeze-dried substance were chromatographed on Sephadex LH 20$^{(R)}$ (column 100 × 2.5 cm) in the system glacial acetic acid/-butanol/water (2:4:20). 228 mg of a pure fraction were isolated.

Amino-acid analysis: ratio Gly:Glu = 6 : 8.5 (theory 6:8).

EXAMPLE 2

Trypsin-callicrein inhibitor penta-(Glu-Glu-OH)

900 mg of penta-Boc-trypsin-callicrein inhibitor were reacted with 625 mg (1.3 mmoles) of HCl.H-Glu(OBu$^t$)-Glu(OB$^t$)-OBu$^t$ in a manner analogous to that described in Example 1. After treatment with trifluoroacetic acid and subsequent dialysis, 770.4 mg of raw substance were obtained. 500 mg of this raw substance were purified as described in Example 1.

Yield: 382 mg of a pure fraction.
Amino-acid analysis: ratio Gly:Glu = 6 : 14.6 (theory 6:13).

EXAMPLE 3

Trypsin-callicrein inhibitor penta-(Glu-Glu-Glu-OH)

900 mg of penta-Boc-trypsin-callicrein inhibitor were reacted with 867 mg (1.3 mmoles) of HCl.H-Glu(OBu$^t$)-Glu(OBu$^t$)-Glu(OBu$^t$)-OBu$^t$ in a manner analogous to that described in Example 1. After treatment with trifluoroacetic acid, 1.355 g of raw substance were obtained which were chromatographed in 0.1 m acetic acid over Sephadex G 25 $^{(R)}$ (column 200 × 4 cm).

Yield: 674.9 mg of a pure fraction.
Amino-acid analysis: ratio Gly:Glu = 6 : 18.3 (theory 6:18).

EXAMPLE 4

Trypsin-callicrein inhibitor penta-(Glu-Glu-Glu-Glu-OH)

900 mg of penta-Boc-trypsin-callicrein inhibitor were reacted with 1.11 g (1.3 mmoles) of HCl.H-Glu(OBu$^t$)-Glu(OBu$^t$)-Glu(OBu$^t$)-Glu(OBu$^t$)-OBu$^t$ in a manner analogous to that described in Example 1. After treatment with trifluoroacetic acid, 1.15 g of raw substance were obtained which were chromatographed in 0.1 m acetic acid over Sephadex G 25 $^{(R)}$ (column 200 × 4 cm).

Yield: 745 mg of a pure fraction.
Amino-acid analysis: ratio Gly:Glu = 6 : 23.4 (theory 6:23).

EXAMPLE 5

Trypsin-callicrein inhibitor penta-aspartic acid 900 mg of penta-Boc-trypsin-callicrein inhibitor were reacted with 365 mg (1.3 mmoles) of HCl.H-Asp(OBu$^t$)-OBu$^t$ in a manner analogous to that described in Example 1. After treatment with trifluoroacetic acid, 1.083 g of raw substance were obttained which were chromatographed in 0.1 m acetic acid over Sephadex G 25 $^{(R)}$ (column 200 × 4 cm).

Yield: 707.6 mg of a pure fraction.
Amino-acid analysis: ratio Gly:Glu:Asp = 6 : 3.2 : 10.5 (thery 6:3:10).

EXAMPLE 6

Trypsin-callicrein inhibitor penta-(Glu-Asp-OH)

900 mg of penta-Boc-trypsin-callicrein inhibitor were reacted with 610 mg (1.3 mmoles) of HCl.H-Glu(OBu$^t$)-Asp(OBu$^t$)-OBu$^t$ in a manner analogous to that described in Example 1. After treatment with trifluoroacetic acid, 1.1 g of raw substance were obtained whicch were chromatographed in 0.1 m acetic acid over Sephadex G 25 $^{(R)}$ (column 200 × 4 cm).

Yield: 759.3 mg of a pure fraction.
Amino-acid analysis: ratio Gly:Glu:Asp = 6.0 : 8.5 : 10.5 (theory 6:8:10).

EXAMPLE 7

Trypsin-callicrein inhibitor penta-(Glu-Glu-Asp)

900 mg of penta-Boc-trypsin-callicrein inhibitor were reacted with 848 mg (1.3 mmoles) of HCl.H-Glu(OBu$^t$)-Glu(OBu$^t$)-Asp(OBu$^t$)-OBu$^t$ in a manner analogous to that described in Example 1. After treatment with trifluoroacetic acid, 1.266 g of raw substance were obtained which were chromatographed in 0.1 m acetic acid over Sephadex G 25$^{(R)}$ (column 200 × 4 cm).

Yield: 727 mg of a pure fraction.
Amino-acid analysis: ratio Gly:Glu:Asp = 5.5 : 13.6 : 10.0 (theory 6:13:10).

EXAMPLE 8

Trypsin-callicrein inhibitor penta-(Asp-Glu-Asp)

900 mg of penta-Boc-trypsin-callicrein inhibitor were reacted with 830 mg (1.3 mmoles) of HCl.H-Asp(OBu$^t$)-Glu(OBu$^t$)-Asp(OBu$^t$)-OBu$^t$ in a manner analogous to that described in Example 1. After treatment with trifluoroacetic acid, 1.25 g of raw substance were obtained which were chromatographed in 0.1 m acetic acid over Sephadex G 25$^{(R)}$ (column 200 × 4 cm).

Yield: 628.4 mg of a pure fraction.
Amino-acid analysis: ratio Gly:Glu:Asp = 6.0 : 8.0 :15.1 (theory 6:8:15).

EXAMPLE 9

Trypsin-callicrein inhibitor penta(Glu-Asp-Glu-Asp)

900 mg of penta-Boc-trypsin-callicrein inhibitor were reacted with 1.07 g (1.3 mmoles) of HCl.H-Glu(OBu$^t$)-Asp(OBu$^t$)-Glu(OBu$^t$)-Asp(OBu$^t$)-OBu$^t$ in a manner analogous to that described in Example 1. After treatment with trifluoroacetic acid, 1.54 g of raw substance were obtained which were chromatographed in 0.1 m acetic acid over Sephadex G 25$^{(R)}$ (column 200 × 4 cm).

Yield: 634 mg of a pure fraction.
Amino-acid analysis: ratio Gly:Glu:Asp = 5.7 : 13.0 : 15.6 (theory 6:13:15).

EXAMPLE 10

Trypsin-callicrein inhibitor penta-(Glu-D-Glu-OMe)

900 mg of penta-Boc-trypsin-callicrein inhibitor were reacted with 597 mg (1.3 mmoles) of HCl.H-

Glu(OBu$^t$)-D-Glu(OBu$^t$)-OMe (J. Chem. Soc. Perkin I 1972, page 1) in a manner analogous to that described in Example 1. After treatment with trifluoroacetic acid, 1.2 g of raw substance was obtained which was chromatographed in 0.1 m acetic acid over Sephadex G 25$^{(R)}$ (column 200 × 4 cm).

Yield: 654 mg of a pure fraction.

Amino-acid analysis: ratio Gly:Glu = 6 : 13.7 (theory 6 : 13).

EXAMPLE 11

Trypsin-callicrein inhibitor penta(Asp-Glu-NH$_2$)

900 mg of penta-Boc-trypsin-callicrein inhibitor were reacted with 533 mg (1.3 mmoles) of HCl.H-Asp(OBu$^t$)-Glu(OBu$^t$)-NH$_2$ (obtained by catalytic hydrogenation of Z-Asp(OBu$^t$)-Glu(OBu$^t$)-NH$_2$, which is described in J. Chem. Soc. C (1968),page 531, in a manner analogous to that described in Example 1. After treatment with trifluoroacetic acid, 1.18 g of raw substance was obtained, which was chromatographed in 0.1 m acetic acid over Sephadex G 25$^{(R)}$ (column 200 × 4 cm).

Yield: 640 mg of a pure fraction.

Amino-acid analysis: ratio Gly:Glu:Asp = 6.0 : 8.6 : 10.3 (theory 6:8:10).

EXAMPLE 12

Trypsin-callicrein inhibitor penta-(Asp-Ser-Asp-OH)

900 mg of penta-Boc-trypsin-callicrein inhibitor were reacted witth 702 mg (1.3 mmoles) of HCl.H-Asp(OBu$^t$)-Ser-Asp(OBu$^t$) (J. Chem. Soc. C, Org., 1969, page 2218) in a manner analogous to that described in Example 1. After treatment with trifluoroacetic acid, 1.3 g of raw substance were obtained which were chromatographed in 0.1 m acetic acid over Sephadex G 25$^{(R)}$ (column 200 × 4 cm).

Yield: 710 mg of a pure fraction.

Amino-acid analysis: ratio Gly:Asp:Ser = 6 : 15.5 : 4.9 (theory 6:15:6).

EXAMPLE 13

Trypsin-callicrein inhibitor penta(Glu-Glu-D-Glu-OH)

900 mg of penta-Boc-trypsin-callicrein inhibitor were reacted witth 867 mg (1.3 mmoles) of HCl.H-Glu(OBu$^t$)-Glu(OBu$^t$)-D-Glu(OBu$^t$)-OBu$^t$ in a manner analogous to that described in Example 1. After treatment with trifluoroacetic acid, 1.25 g of raw substance were obtained which were chromatographed over Sephadex G 25$^{(R)}$ (column 200 × 4 cm).

Yield: 683.2 mg of a pure fraction.

Amino-acid analysis: ratio Gly:Glu = 6.00 : 18.07 (theory 6:18).

EXAMPLE 14

Trypsin-callicrein inhibitor penta-(D-Glu-D-Glu-D-Glu-OH)

900 mg of penta-Boc-trypsin-callicrein inhibitor were reacted witth 867 mg (1.3 mmoles) of HCl.H-D-Glu(OBu$^t$)-D-Glu(OBu$^t$)-D-Glu(OBu$^t$)-OBu$^t$ in a manner analogous to that described in Example 1. After treatment with trifluoroacetic acid, 1.52 g of raw substance were obtained which were chromatographed in 0.1 m acetic acid over Sephadex G 25$^{(R)}$ (column 200 × 4 cm).

Yield: 652.9 mg of a pure fraction.

Amino-acid analysis: ratio Gly:Glu = 6 : 18.88 (theory 6:18).

Preparation of the starting substances a. Z-Glu(OBu$^t$)-Glu(OBu$^t$)-OBu$^t$ 10.4 g (20 mmoles) of Z-Glu(OBu$^t$)-OH.DCHA were stirred into 100 ml of ether and 20 ml of 1N H$_2$SO$_4$ at 0° C. The ether phase was dried with sodium sulfate and concentrated. The residue was dissolved in 50 ml of dimethylformamide. This solution was combined with 5.91 g (20 mmoles) of HCl.H-Glu(OBu$^t$)-OBu$^t$, 2.7 g (20 mmoles) of HOBt, 2.6 ml of N-ethylmorpholine and, at 0° C, 4.4 g of DCC (as a solution in dimethylformamide). The whole was stirred for 1 hour 0° C, for 2 hours at room temperature and allowed to stand overnight at room temperature. The next day, the precipitate was filtered off with suction and the filtrate was concentrated. The residue was dissolved in ethyl acetate and the solution was washed successively with NaHCO$_3$ solution, KHSO$_4$ solution, NaHCO$_3$ solution and water, dried over sodium sulfate and concentrated. The residue was chromatographed in ethyl acetate over about 30 g of basic Al$_2$O$_3$ (Woelm, activity degree I). The eluate was cconcentrated and dried in a high vacuum. Yield: 10 g of oil (86 %). After some time, the oil crystallized; melting point 88° C.

C$_{30}$H$_{46}$N$_2$O$_9$ (578.7): Calc.: C, 62.26; H, 8.01; N, 4.84; Found: C, 62.3; H, 8.1; N, 5.1.

b. HCl.H-Glu(OBu$^t$)-Glu(OBu$^t$)-OBu$^t$ 9.6 g of Z-Glu(OBu$^t$)-Glu(OBu$^t$)-OBu$^t$ were dissolved in methanol, combined with a Pd catalyst and hydrogenated with the aid of an autotitrator with addition off 2N-methanolic HCl at pH 4.5. When the hydrogenation was completed, the catalyst was filtered off with suction and the filtrate was concentrated.

Yield: 7.3 g of oil 91 %).

C$_{22}$H$_{40}$N$_2$O$_7$.HCl (481.04)

c. Z-Glu(OBu$^t$)-Glu(OBu$^t$)-Glu(OBu$^t$)-OBu$^t$ 6.65 g (12.9 mmoles) of Z-Glu(OBu$^t$)-OTcp were added to a solution of 6.2 g (12.9 mmoles) of HCl.H-Glu(OBu$^t$)-Glu(OBu$^t$)-OBu$^t$, 1.74 g (12.9 mmoles) of HOBt, 1.68 ml (12 mmoles) of N-ethylmorpholine in 60 ml of dimethylformamide, the whole was stirred for 5 minutes and concentrated in a high vacuum. The residue was dissolved in ethyl acetate and treated as described under (a). After drying over sodium sulfate, the solution was concentrated and the residue was triturated with petroleum ether. The whole was cooled to 0° C and filtered with suction. Yield: 6.3 g (70 %). Melting point: 111° to 113° C.

$[\alpha]_D^{22} = -29.8°$ (c = 1, methanol)

C$_{39}$H$_{61}$N$_3$O$_{12}$ (763.94): Calc.: C, 61.35; H, 8.04; N, 5.51. Found: C, 61.2; H, 8.0; N, 5.6.

d. HCl.H-Glu(OBu$^t$)-Glu(OBu$^t$)-Glu(OBu$^t$)-OBu$^t$ 5.8 g (7.6 mmoles) of Z-Glu(OBu$^t$)-Glu(OBu$^t$)-Glu(OBu$^t$)-OBu$^t$ were hydrogenated in methanol as described under (b). Yield: 4.8 g of oil (95 %).

C$_{31}$H$_{55}$N$_3$O$_{10}$ . HCl (666.3)

e. Z-Glu(OBu$^t$)-Glu(OBu$^t$)-Glu(OBu$^t$)-Glu(OBu$^t$)-OBu$^t$ 3.05 g (5.85 mmoles) of Z-Glu(OBu$^t$)-OTcp were added to a solution of 3.9 g (5.85 mmoles) of HCl.H-Glu(OB$^t$)-Glu(OBu$^t$)-Glu(OBu$^t$)-OBu$^t$, 0.79 g (5.85 mmoles) of HOBt and 0.76 ml (5.85 mmoles) of N,ethylmorpholine in 50 ml of dimethylformamide. The whole was stirred for 1 hour at room temperature and worked up as described under (c). Yield: 4.75 g (86 %). Melting point: 119° to 120° C.

$[\alpha]_D^{22} = 29.1°$ (c = 1, methanol)

$C_{48}H_{76}N_4O_{15}$ (949.2): Calc.: C, 60.75; H, 8.08; N, 5.91. Found: C, 60.6; H, 8.0; N, 5.8.

f. HCl.H-Glu(OBu$^t$)-Glu(OBu$^t$)-Glu(OBu$^t$)-Glu(OBu$^t$)-OBU$^t$ 4.4 g (4,63 mmoles) of Z-Glu(OBu$^t$)-Glu(OBu$^t$)-Glu(OBu$^t$)-Glu(OBu$^t$)-OBu$^t$ were hydrogenated catalytically in methanol as descibed under (b). Yield:3.85 g of oil (98 %).

$C_{40}H_{70}N_4O_{13}$. HCl (851.5)

g. Z-Glu(OBu$^t$)-Asp(OBu$^t$)-OBu$^t$ 52 g (0.1 mmoles) of Z-Glu(OBu$^t$)-OH.DCHA were stirred at 0° C in ether and 100 ml of 1N-H$_2$SO$_4$. The ether phase was washed once with water, dried over sodium sulfate and concentrated. The residue was dissolved in 200 ml of dimethylformamide. This solution was combined with 28.1 g (0.1 mole) of HCl.H-Asp(OBu$^t$)-OBu$^t$, 13.5 g of HOBt (0.1 mole), 13 ml of N-ethylmorpholine (0.1 mole) and, at 0° C, with 22 g of DCC (as solution in dimethylformamide). The process was then carried out as described under a). The residue crystallized upon trituration with petroleum ether. Yield: 42.9 g (76 %); melting point: 128 to 130° C. For further purification, the substance was dissolved in ether and chromatographed over 120 g of basic Al$_2$O$_3$. Yield: 34.7 g; melting point 131° to 132° C.

$[\alpha]_D^{22} = -17.9°$ (c = 1, methanol)

$C_{29}H_{44}N_2O_9$ (564.7): Calc.: C, 61.70; H, 7.86; N, 4.96. Found: C, 61.7; H, 7.8; N, 4.9.

h. HCl.H-Glu(OBu$^t$)-Asp(OBu$^t$)-OBu$^t$ 34.5 g (62 mmoles) of Z-Glu(OBu$^t$)-Asp(OBu$^t$)-OBu$^t$ were hydrogenated catalytically in methanol as described under (b). Yield: 29.3 g of oil (100 %).

$C_{21}H_{38}N_2O_7$ . HCl (467.01)

i. Z-Glu(OBu$^t$)-Glu(OBu$^t$)-Asp(OBu$^t$)-OBu$^t$ 13.82 g (26.7 mmoles) of Z-Glu(OBu$^t$)-OTcp were added at room temperature to a solution of 12.5 g (26.7 mmoles) of HCl.H-Glu(OBu$^t$)-Asp(OBu$^t$)-OBu$^t$, 3.6 g (26.7 mmoles) of HOBt, 3.5 ml (26.7 mmoles) of N-ethylmorpholine in 100 ml of dimethylformamide. The whole was allowed to stand for 1 hour and worked up as described under (c). Yield: 27.4 g of oil. For further purification, the oil was dissolved in ether and chromatographed over 75 g of basic Al$_2$O$_3$.

Yield: 17.65 g of amorphous mass (88 %).

$[\alpha]_D^{22} = -23.9°$ (c = 1, methanol).

$C_{38}H_{59}N_3O_{12}$ (749.9): Calc.: C, 60.86; H, 7.93; N, 5.61. Found: C, 60.3; H, 7.9; N, 5.6.

j. HCl.H-Glu(OBu$^t$)-Glu(OBu$^t$)-Asp(OBu$^t$)-OBu$^t$ 17 g (22.7 mmoles) of Z-Glu(OBu$^t$)-Glu(OBu$^t$)-Asp(OBu$^t$)-OBu$^t$ were hydrogenated catalytically in methanol in a manner analogous to that described under (b).

Yield: 14.34 g of amorphous mass (97 %)

$C_{30}H_{53}N_3O_{10}$ . HCl (652.2)

k. Z-Asp(OBu$^t$)-Glu(OBu$^t$)-Asp(OBu$^t$)-OBu$^t$ 11.25 ml (26.7 mmoles) of Z-Asp(OBu$^t$)-ONSu were added to a solution of 12.5 g (26.7 mmoles) of HCl.H-Glu(OBu$^t$)-Asp(OBu$^t$)-OBu$^t$ and 3.5 ml (26.7 mmoles) of N-ethylmorpholine in 100 ml of dimethylformamide and the whole was allowed to react for about 20 hours at room temperature. Working up was effected as described under (c). For purification, the residue was dissolved in ether and chromatographed over 50 g of basic Al$_2$O$_3$.

Yield: 13.4 g of amorphous substance (68 %).

$[\alpha]_D^{22} = -23.9°$ (c = 1, methanol)

$C_{37}H_{57}N_3O_{12}$ (735.9): Calc.: C, 60.4; H, 7.81; N, 5.71. Found: C, 60.0; H, 7.1; N, 5.6.

l. HCl.H-Asp(OBu$^t$)-Glu(OBu$^t$)-Asp(OBu$^t$)-OBu$^t$ 12.8 g (17.4 mmoles) of Z-Asp(OBu$^t$)-Glu(OBu$^t$)-Asp(OBu$^t$)-OBu$^t$ were hydrogenated catalytically in methanol in a manner analogous to that described under (b).

Yield: 10.4 g of amorphous substance (94 %).

$C_{29}H_{51}N_3O_{10}$ . HCl (638.2)

m. Z-Glu(OBu$^t$)-Asp(OBu$^t$)-Glu(OBu$^t$)-Asp(OBu$^t$)-OBu$^t$ 5 g (10 mmoles) of Z-Glu(OBu$^t$)-OTcp were added to a solution of 6.4 g (10 mmoles) of HCl.H-Asp(OBu$^t$)-Glu(OBu$^t$)-Asp(OBu$^t$)-OBu$^t$, 1.35 g (10 mmoles) of HOBt and 1.3 ml (10 mmoles) of N-ethylmorpholine in 40 ml of dimethylformamide, the whole was stirred for 1 hour at room temperature and worked up in a manner analogous to that described under (c). The residue was triturated with petroleum ether. Yield: 7.4 g (80 %); melting point 196° C.

$[\alpha]_D^{22} = -24.6°$ (c = 1, methanol)

$C_{46}H_{72}N_4O_{15}$ (921.1): Calc.: C, 59.98; H, 7.88; N, 6.08. Found: C, 59.6; H, 7.8; N, 6.1.

n. HCl.H-Glu(OBu$^t$)-Asp(OBu$^t$)-Glu(OBu$^t$)-Asp(OBu$^t$)-OBu$^t$ 7 g (7.6 mmoles) of Z-Glu(OBu$^t$)-Asp(OBu$^t$)-Glu(OBu$^t$)-Asp(OBu$^t$)-OBu$^t$ were hydrogenated catalytically in methanol as described under (b).

Yield: 6.1 g of amorphous substance (97.5 %)

$C_{38}H_{66}N_4O_{13}$ . HCl (823.4)

o. Penta-Boc-trypsin-callicrein inhibitor

α. 1.3 g of trypsin-callicrein inhibitor were dissolved in 10 ml of water. The solution was combined with 50 ml of dimethylformamide and 4.4 ml of saturated NaHCO$_3$ solution. Then, 430 mg of Boc-ONSu were added, the whole was stirred for 1 hour at room temperature and allowed to stand overnight. The next day, it was acidified to pH 5 with 2N-acetic acid. The clear solution was concentrated in a high vacuum. The residue was tritured with water, filtered off with suction, well washed with water and dried. It was again triturated with ethyl acetate, filtered off with suction and dried. Yield 880 mg.

Paper electrophoresis showed, in an acid medium, a uniform substance which was different from the trypsin-callicrein inhibitor.

β. 1.3 g of trypsin-callicrein inhibitor were suspended in 20 ml of di-methylformamide. This suspension was combined with 270 mg of HOBt, 480 mg of Boc-ONp and 0.14 ml of 1,1',4,4'-tetramethylguanidine. Further 0.7 ml of 1,1'-4,4'-tetramethylguanidine and 480 mg of Boc-ONp were added in several portions. The whole was stirred for a total of 2 days at room temperature, concentrated and the residue was stirred with ethyl acetate. The precipitate was triturated with methanol and filtered off with suction. Yield: 950 mg. The product so obtained was found to be identical in paper electrophoresis with the product obtained according to (α).

γ. 7 g of trypsin-callicrein inhibitor were dissolved in 77 ml of water. 315 ml of dimethylformamide, 24 ml of saturated NaHCO$_3$ solution and 14 ml of Boc-azide were added. The whole was stirred for 5 hours at 35° C, acidified with 2N-acetic acid to pH 5 and concentrated in a high vacuum. The residue was triturated with water and filtered off with suction. Yield: 6.5 g. Th product obtained was found to be identical in paper electrophoresis with the substance obtained according to (α).

p. HCl.H-D-Glu(OBu$^t$)-D-Glu(OBu$^t$)-D-Glu(OBu$^t$)-OBu$^t$

The compound was prepared according to the methods described under (a), (b), (c) and (d) from the corresponding D-glutamic acid derivatives. The melting points corresponded to those of the L-compounds. The specific rotations of the D-compounds were also fouund to correspond in their values to those of the L-compounds, but had a reversed sign.

q. Z-Glu(OBu$^t$)-D-Glu(OBu$^t$)-OBu$^t$ 5.17 g of Z-Glu(OBu$^t$)-OTcp and 2.6 ml of N-ethylmorpholine were added to a solution of 2.96 g (10 mmoles) of HCl.H-D-Glu(OBu$^t$)-OBu$^t$ and 1.35 g of HOBt in 20 ml of dimethylformamide. After 1 hour, the whole was concentrated, the residue was dissolved in ethyl acetate and washed with water, saturated NaHCO$_3$ solution, KHSO$_4$ solution and NaHCO$_3$ solution, dried over Na$_2$SO$_4$ and concentrated. For purification, it was chromatographed in methylene chloride over 70 g of silica gel. After elution with 400 ml of methylene chloride, the substance was eluted with the methylene chloride/acetone mixture (9:1). Yield: 5.3 g of oil.

n. HCl.H-Glu(OBu$^t$)-D-Glu(OBu$^t$)-OBu$^t$ 5.3 g of oily Z-Glu(OBu$^t$)-D-Glu(OBu$^t$)-OBu$^t$ were hydrogenated catalytically in a manner analogous to that of Example (b). Yield: 3.64 g of oil.

s. Z-Glu(OBu$^t$)-Glu(OBu$^t$)-D-Glu(OBu$^t$)-OBu$^t$ 0.97 ml of N-ethylmorpholine and 3.88 g of Z-Glu(OBu$^t$)OTcp were added to a solution of 3.6 g of HCl.H-Glu(OBu$^t$)-D-Glu(OBu$^t$)-OBu$^t$ and 1.01 g of HOBt in 20 ml of dimethylformamide. After 1 hour, the product was worked up in a manner analogous to that of Example (c). Yield: 4.35 g; melting point 129° to 130° C.

$[\alpha]_D^{22} = -10.4°$ (c = 1, in methanol)

t. HCl.H-Glu(OBu$^t$)-Glu(OBu$^t$)-D-Glu(OBu$^t$)-OBu$^t$ 4.13 g of Z-Glu(OBu$^t$)-Glu(OBu$^t$)-D-Glu(OBu$^t$)-OBu$^t$ were hydrogenated catalytically in a manner analogous to that of Example (b). Yield: 3.3 g of amorphous substance.

Abbreviations

| | |
|---|---|
| Boc | tert.-Butyloxycarbonyl |
| Z | Benzyloxycarbonyl |
| OBu$^t$ | tert.-Butyl ester |
| ONp | 4-Nitrophenyl ester |
| ONSu | N-Hydroxysuccinimide ester |
| OTcp | 2,4,5-Trichlorophenyl ester |
| DCHA | Dicyclohexylamine |
| DCC | Dicyclohexyl-carbodiimide |
| HOBt | 1-Hydroxybenzotriazole |

We claim:

1. Modified trypsin-callicrein inhibitor wherein the five carboxyl groups present in the unmodified material are amidated by peptide groups of the formula —R(R)$_x$W, wherein R' is

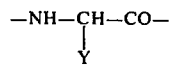

or prolyl; Y is hydrogen, alkyl having 1 to 5 carbon atoms, or alkyl having 1 to 5 carbon atoms substituted by a carboxyl, hydroxyl, or carbonamide group; X is an integer from 0 to 10 such that, if X = 0, then R is

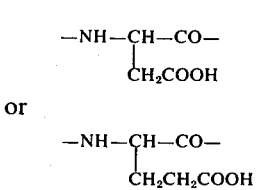

and, if X is an integer from 1 to 10, then at least one R is

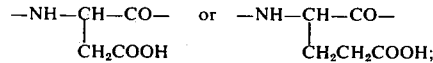

and W is —OH, —NH$_2$, —NHC$_2$H$_5$, —OCH$_3$, or —OC$_2$H$_5$ when —R(R)$_x$— contains at least two

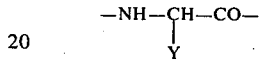

wherein Y contains carboxy, but is otherwise —OH.

2. A method for making a modified amidated trypsin-callicrein inhibitor as in claim 1 which comprises reacting, in the presence of 1-hydroxy-benzotriazole and dicyclohexylcarbodiimide,
   a. trypsin-callicrein inhibitor, the five primary amino groups of which are each protected by an acid-cleavable amino-protective group, with
   b. an amino acid or peptide of the formula H$_2$N-R'(-R')$_x$W', wherein R' is

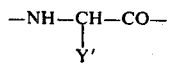

or prolyl, Y' is hydrogen, alkyl having 1 to 5 carbon atoms, or alkyl having 1 to 5 carbon atoms substituted by a t-butyl carboxylate, hydroxyl, or carbonamide group; X is an integer from 0 to 10 such that, if X = 0, then R' is

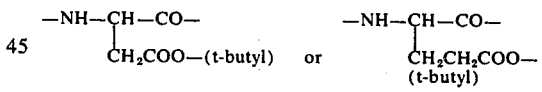

and, if X is an integer from 1 to 10, then at least one R' is

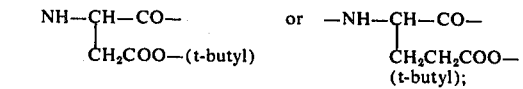

and W' is —O-(t-butyl), —NH$_2$, —NHCH$_3$, —NHC$_2$H$_5$, —OCH$_3$, or —OC$_2$H$_5$ when —R'(R')$_x$— contains at least two

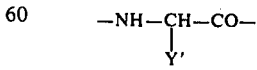

wherein Y' contains t-butyl carboxylate, but is otherwise —O-(t-butyl), and then cleaving said amino-protective groups from the product with acid to give said modified trypsin-callicrein inhibitor.

* * * * *